United States Patent [19]

Barron et al.

[11] 4,213,183

[45] Jul. 15, 1980

[54] SYSTEM FOR NONDESTRUCTIVE EVALUATION OF MATERIAL FLAW CHARACTERISTICS

[75] Inventors: Roger L. Barron, Annandale, Va.; Anthony N. Mucciardi, Silver Spring, Md.; Claire L. Brown, Vienna, Va.

[73] Assignee: Adaptronics, Inc., McLean, Va.

[21] Appl. No.: 22,753

[22] Filed: Mar. 22, 1979

Related U.S. Application Data

[63] Continuation of Ser. No. 838,169, Sep. 30, 1977, abandoned, which is a continuation-in-part of Ser. No. 825,107, Aug. 16, 1977, abandoned.

[51] Int. Cl.$^2$ ............................................. G01N 29/04
[52] U.S. Cl. ....................................... 364/507; 73/634; 364/487; 364/552
[58] Field of Search ............... 364/507, 524, 552, 487, 364/498, 415, 416; 73/618, 619, 632, 634; 356/237; 209/528

[56] References Cited

U.S. PATENT DOCUMENTS

| | | | |
|---|---|---|---|
| 3,534,590 | 10/1970 | Kent et al. | 73/618 |
| 3,771,355 | 11/1973 | Sachs | 73/618 |
| 3,898,838 | 8/1975 | Connelly | 73/634 |
| 3,910,124 | 10/1975 | Halsey | 73/618 |
| 3,978,714 | 9/1976 | Shraiber et al. | 73/634 |
| 4,062,237 | 12/1977 | Fox | 364/416 |
| 4,063,549 | 12/1977 | Beretsky | 364/415 |

*Primary Examiner*—Errol A. Krass
*Attorney, Agent, or Firm*—Jay M. Cantor

[57] ABSTRACT

The disclosure relates to a system for nondestructive evaluation (NDE) of material flaw characteristics. The NDE system, after being trained on previously-acquired experimental data, is given an assigned NDE task by the inspector and/or remote observer. This task is requested via a small keyboard on the system control unit or remotely. The system then issues detailed commands to stepping motors in its transducer-positioning mechanism (scanner) and to logic circuits in the ultrasonic (UT) pulser/receiver to establish the sequence of transducer (probe) translation and orientation changes and the frequency, pulse-width, and pulse repetition interval used to energize the probe. Shaft-position encoders in the scanning mechanism are used to insure faithful following of the commanded position/orientation sequence. Additionally, the system establishes a sequence of windowing functions to be used for time-gating of the output waveform from the probe, and it calls from memory and performs the appropriate signal processing functions for the assigned inspection task.

The signal processing unit within the system detects, classifies, and sizes flaws on or within the object under test by use of adaptive learning network (ALN) signal-processing functions. This unit causes the display to present appropriate information on suspected flaws for evaluation by the inspector and/or remote observer. The display unit also has a miniature printer to make permanent hardcopy records of vital information. Data storage is provided for retention of those waveforms and related data of greatest interest.

22 Claims, 7 Drawing Figures

SYSTEM FOR NONDESTRUCTIVE EVALUATION OF MATERIAL FLAW CHARACTERISTICS

PRIOR APPLICATIONS

This application is a continuation of our prior application, Ser. No. 838,169, filed Sept. 30, 1977 now abandoned, which is a continuation-in-part of our prior application Ser. No. 825,107, filed Aug. 16, 1977, now abandoned.

BACKGROUND

This invention relates to a system for nondestructive testing and evaluation of material flaw characteristics. Modern technology places increasing demands on nondestructive evaluation (NDE) capabilities. In large measure these capabilities depend upon methods for non-invasive inspection of the interior of critical structures. It is necessary to infer the presence or absence of structural defects by interpretation of the energy emitted by or, more usually, reflected from these defects. Many forms of energy sources exist for NDE applications, including ultrasonic, eddy current, and electromagnetic, to name the most commonly used. However, in the prior art, interpretation of the waveforms of the emitted or reflected energy has been unsophisticated.

For example, the almost universal practice in acoustic emission monitoring has been to monitor the cumulative number and rapidity of pulse-like acoustic emissions from structures as their loads are applied. Little attention has been directed to consideration of the waveform shapes of the acoustic pulses, which may convey vital information about the true integrity of structures. As a further example, ultrasonic pulse-echo testing has relied almost entirely on just one parameter of reflected ultrasonic waveforms: amplitude. This is somewhat analogous to a mother trying to judge if her baby is ill by how loudly the infant cries. Amplitude can be indicative in some cases, but very misleading in others. Recent theoretical and experimental evidence in NDE research and development shows clearly that the reflected waveform shape, or, more expressly, the waveform frequency content of an ultrasonic echo, is much more significant as an indicator of the presence of a defect than is the amplitude.

Use of information in the shapes of NDE waveforms requires test-instrument systems and procedures not found in the prior NDE art. Of particular importance in the new art is realization of a high degree of automaticity, because human inspectors are not generally able to interpret the greatly increased quantity of data involved in waveform shape analyses. The achievement of automatic interpretation of NDE waveforms is a major thrust of the present invention.

This automatic interpretation capability is not limited to NDE applications, although those are extensive. The techniques of the present invention can be used anywhere when given events (waveform sources) and the resulting waveforms are uniquely and repeatedly related. Thus, the interpretation of physiological waveforms falls within the purview of our invention, as do processes in seismology, remote sensing of intruders, diagnoses of the condition of motor vehicles, and numerous other arts and disciplines.

Accordingly, NDE applications are discussed in the present disclosure by way of illustration but not limitation.

Likewise, there are many NDE applications envisioned by the inventors hereof. For example, in the aviation industry, the detection and sizing of underfastener cracks are critical inspection problems in airframe and turbine disk testing. For such, the NDE instrument system of the present invention enhances inspections because it provides: (1) ability to detect smaller defects than before, (2) quantitative measurements of defect sizes and orientations, (3) increased speed of inspection, and (4) reduced reliance on skill of the inspector. Other pressing needs in aeronautics and in weapons fabrication include inspection of adhesively bonded structures to detect and classify bond defects such as disbonds, delaminations, and bond porosity, and to infer the strength of bonds from parameters of ultrasonic signals.

The area to be used as the primary basis for discussion in this disclosure is the inservice inspection (ISI) of piping, nozzles, and pressure vessels. This embraces NDE applications for pipelines, boilers of all kinds, and the facilities used in fossil-fueled and nuclear-power generating plants. Several very critical ISI problem areas exist in these applications, among them:

(1) inspection for cracks and faulty welds in gas and petroleum pipelines;

(2) inspection of steam tubing for cracking, pitting, high-cycle fatigue, and denting (Denting is the term used to refer to the outcome of a corrosion process occurring on the secondary side of a steam generator-corrosion products build up in the crevice region between the tube outer surface and the surfaces of supporting plates; as the thickness of these deposits grows the tube is compressed; cracks can occur in the tube and in the support plates.);

(3) inspection for cracks in welds and weld heat-affected zones in piping for nuclear power generating and other plants (The welds may involve bi- and tri-metallic junctions.);

(4) inspection for inner-diameter cracks produced by intergranular stress-assisted corrosion cracking and by other causes in piping for nuclear power generating plants and other plants;

(5) inspection for inner-radius cracks in the parent metal and in cladding (where used) of feedwater nozzles, control-rod drive nozzles, and other nozzles of nuclear power generating and other plants; and (6) inspections of reactor and other pressure vessels. The motivation for improvement of ISI technology in the electric power generating industry comes from economic factors, the need to minimize radiation exposure to inspection personnel, the need for increased efficiency and reliability of ISI, and the goal of obtaining licensing credit from regulatory authorities. This is discussed fully in *Planning Support Document for the EPRI Non-destructive Evaluation (NDE) Program*, G. J. Dau, Electric Power Research Institute, Palo Alto, California, Sept. 2, 1977, which states "Experience to date indicates that present practice does not produce results of sufficient accuracy and repeatability to permit reliable flaw identification and classification," and that "... a shortage of skilled operators (inspectors) is imminent." The needed improvement in ISI NDE capabilities for the electric power industry will minimize the inspection time (especially in hostile environments); increase on-line analysis capability; speed up regulatory decisions; provide fast, accurate, reproducible, and unambiguous results to limit the escalation of test and inspection requirements; and prevent downtime via early warnings of material degradations and simplifying the inspection procedures, as skilled personnel are in short supply.

Presently, materials are ultrasonically (UT) inspected almost entirely by manual means. The human inspector is often in a biologically hostile environment due to heat, radiation, cramped working quarters, etc., yet must be vigilant and skilled in interpreting readings produced by NDE equipment. He must constantly verify correct position and orientation of the UT transducer and that proper coupling is being made between transducer and the object under test to ensure that the appropriate signals are observed.

In present industrial ISI practice, the radio-frequency UT signal is full-wave rectified by the inspector's (portable) receiver and displayed on a cathode ray oscilloscope as a series of spikes. During preinspection calibration tests, the inspector is instructed to report "indications" that are a certain percentage of full-scale height. Thus, the rectified echo amplitude occurring from a certain depth in the material is the basis of present ultrasonic NDE inspection practice. Unfortunately, many frequently-occurring factors can contribute to false indications (false alarms) and to no indications (false dismissals). These factors include inadequate couplant, surface roughness, material anisotropy, weldments in the sound path, delaminations, cladding interfaces, benign reflectors (e.g., material grains, pipe counterbores, and other geometric factors), transducer variations, defect orientations other than normal to the sound beam, defect size variations, etc. Thus, defect detection via visual evaluation of a rectified pulse, recorded under harsh conditions and due to any of the above factors, is an extremely difficult task, even for experienced inspectors. Defect sizing is considerably more difficult.

UT NDE can be made less hazardous to humans and more reliable relative to defect detection and sizing by: (1) an automatic or semiautomatic transducer scanning apparatus to reduce inspector exposure and provide greatly enhanced positioning control; (2) a microcomputer-based signal processor to interpret the RF signals (without necessarily using amplitude as an input parameter) and to mask out the characteristics of different transducers; (3) apparatus for recording the unrectified (i.e., RF) echoes that enable an archieval copy to be made—the UT scan can be replayed later for further analyses, inspector training, and defect growthrate determinations.

These devices must be programmable for flexibility of use and must be integrated functionally within a single system that is physically compact and rugged. Microprocessors and microcomputers are used as interfaces in place of hardwired circuits to permit changes in recording, display, playback, and analysis functions, as conditions require. Adaptive Learning Networks (ALN's) are used to detect defects and discriminate between them and the numerous benign scatterers that produce UT echoes similar to those received from defects.

The above is accomplished in accordance with the hardware scanning control, signal processing, and recording system of the present invention. Briefly, in accordance with the present invention, there is provided a nondestructive evaluation (NDE) system which has considerable accuracy and flexibility. With it, inspection personnel are easily able to perform the above three listed functions. The system uses programmable digital LSI circuitry.

FIG. 3, comprising FIGS. 3A-C, is a block diagram of the hardware in accordance with a preferred embodiment of the invention; and, FIG. 4, comprising

Figure 1:
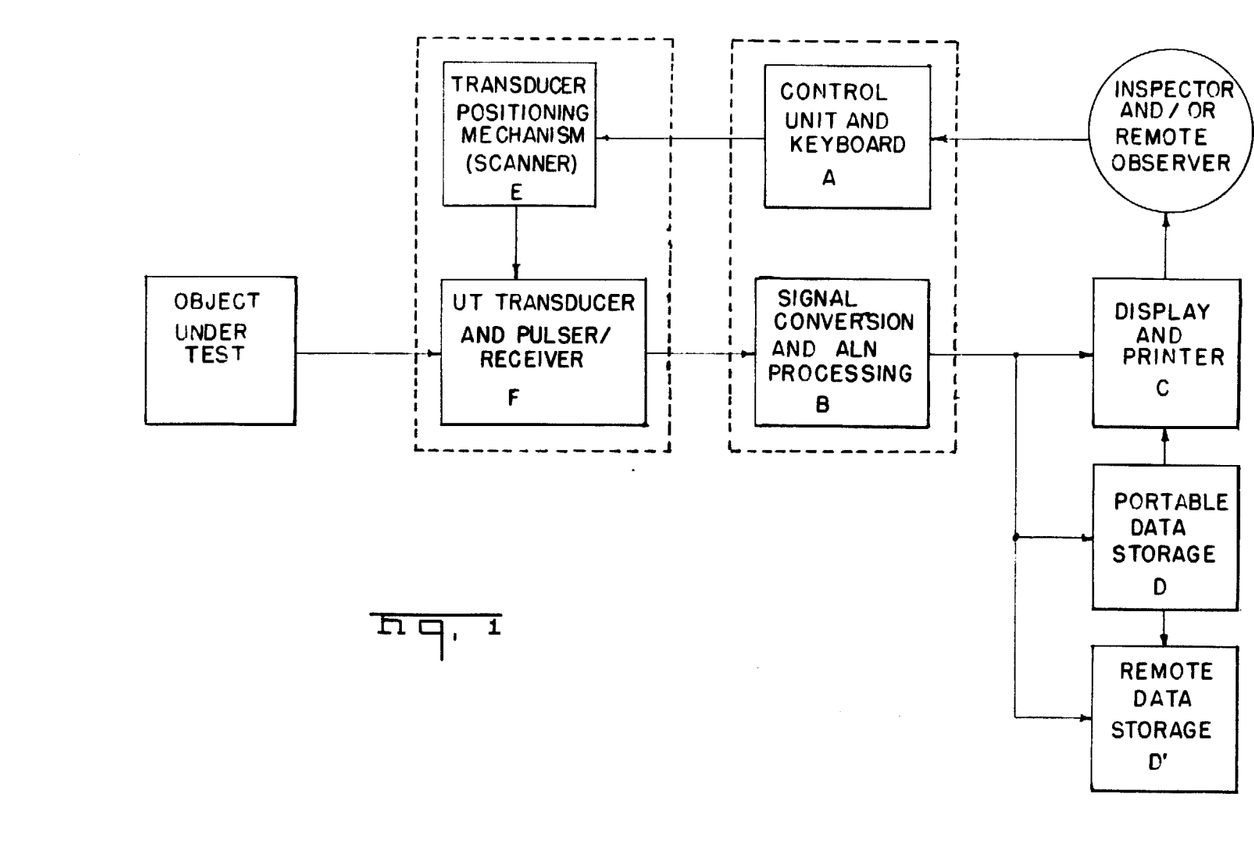
FIG. 1 is a diagram of major subsystems and information flows within this NDE system.

FIG. 1 shows the major subsystems of the nondestructive evaluation (NDE) system, which comprises principally the following subsystems: control unit and keyboard A, signal conversion and ALN processing unit B, display and printer C, data storage units D and D', transducer-positioning mechanism (scanner) E, and UT transducer and pulser/receiver F. The scanner may be used in manual, preprogrammed, or remote-control modes. The scanner contains either a single transducer or array of transducers. This permits either pulse-echo or phased transducer arrays to be used, as will be explained hereinbelow.

In operation, the system is given an assigned inspection task by the inspector and/or remote observer. This task is requested via a small keyboard on the control unit A or remotely. The system then issues detailed commands to stepping motors in the transducer-positioning mechanism (scanner) E and to logic circuits in the pulser-receiver F to establish the sequence of probe translation and orientation changes and the frequency, pulse-width, and pulse repetition interval used to energize the probe. Shaft-position encoders in the scanning mechanism E are used to insure faithful following of the commanded position/orientation sequence. Additionally, the system establishes a sequence of windowing functions to be used for time-gating of the output waveform from the probe, and it calls from memory in A the appropriate ALN structures for the assigned inspection task.

The signal processing unit B detects, locates, and classifies sizes and orientations of flaws on or within the object under test and causes the display C to present appropriate information on these flaws for evaluation by the inspector and/or remote observer. The display unit C also has a miniature printer or similar device to make permanent hard-copy records of vital information. Data storage units D and D' are provided for retention of those waveforms and related data of greatest interest.

A brief discussion of each of the major subsystems within the system follows.

The control unit A supervises the functions of all subsystems within the system. It causes the transducer scanning mechanism E to execute a stored sequence of position and angle changes, receives position and angle information from the scanner readout devices (shaft position encoders), compares this information with the desired coordinates and takes suitable corrective actions if necessary, controls the UT pulser/receiver F, selects suitable time gates for adjusting up to four echo time windows with the signal conversion subsystem digital data buffer, and prepares appropriate header information (i.e., location, depth, ALN(s) used, parameters of UT pulses generated by the system, material under test, surface roughness of object tested, couplant used, test identification number, etc.) to identify each waveform analyzed and/or stored by the system.

The control unit, utilizing programs stored in memory, runs diagnostic tests on portions of the NDE system whenever this system is reset. These diagnostic routines include stepping the motors backward and forward and verifying the movements by reading out the shaft-position encoders. The unit also verifies the correct functioning of the system random access memory and bulk storage devices by writing to and reading back from them. Any deviations from normal operations are displayed to the inspector for appropriate action by him if possible.

The control unit employs a microprocessor with high-level language programming and addressing capabilities (to facilitate convenient communications during program changes). For extensive program changes, the control unit microprocessor is interfaced with a computer terminal having a paper tape reader. But for inputs by the inspector during normal operation of the system, a miniature keyboard on the control unit A is provided. With this keyboard, the inspector defines the type or types of flaws to be detected, including a lower bound on flaw size(s), and the initial transducer position, and transducer orientation, and echo time-window coordinates at which testing is to commence. The inspector may also use the keyboard to override the nominal inspection protocol stored within the instrument memory. For example, he may request more detailed inspection within a given region or the immediate playback and display of specific waveforms from the portable data storage unit.

A central concept in the present invention is the use of this NDE system to acquire information by which its subsequent automatic or semiautomatic operations are made possible. Specifically, the NDE system is caused to record UT waveforms reflected by known (or later determined) defects in representative specimens. These waveforms and the known characteristics of the defects producing them are then input to off-line computer equipment to synthesize appropriate numerical values in the instrument signal-processor subsystem functions. Such numerical values are next entered into the memory elements of the NDE system either manually or via a computer terminal temporarily connected thereto. In this way, the NDE system is programmed to detect and classify flaws in new materials and objects.

The method by which the off-line computer equipment is used to synthesize the NDE system functions from empirically (and, in some cases, theoretically) obtained waveforms for known defects is disclosed in the prior art literature. This literature describes the synthesis of Adaptive Learning Networks (used herein to detect, discriminate, and classify flaws via their UT echo waveforms) and the synthesis of cluster screening functions (herein employed to determine if a received UT echo can be correctly interpreted by existing ALN functions or is so novel as to require further ALN synthesis). Methods for synthesis of Adaptive Learning Networks are fully disclosed in *Cybernetics and the Management of Ecological Systems*, Robinson (Ed.), Spartan Books, New York, 1972, in an article by A. N. Mucciardi entitled "Neuromime Nets as the Basis for the Predictive Component of Robot Brains," pp. 159–193, and other references cited hereinbelow. A method for cluster screening is referenced hereinbelow, and an example thereof is presented in Appendix B.

All of the computer codes needed to implement the NDE system are preferably written and debugged on a microcomputer development system. When the programs are correctly completed, they are "burned" into the erasable, programmable read-only memories (ROM's). These programs include the monitor routines, the scan sequence routines, and the program and processing instructions. The monitor routines are those which handle standard frequently-used sets of instructions such as transferring data to and from the keyboard and display. The scan sequence routines contain all the necessary instructions to control the movements of the transducer scanning mount to any specified positions. The program and processing instructions are those which control the entire sequence of operations, including various options which are used at run time depending on the parameters chosen. Once these programs are "burned" into the ROM's, if at any time they need to be amended, the ROM's can be erased and reprogrammed. All the programs in ROM's are nonvolatile, that is, they remain there regardless of whether the system is on or off. The system random access memory (RAM) and buffer memory are volatile, so the information in them is lost when the power is off. Therefore these RAM memory chips are used solely to hold information which is temporarily stored during run time.

Figure 2:
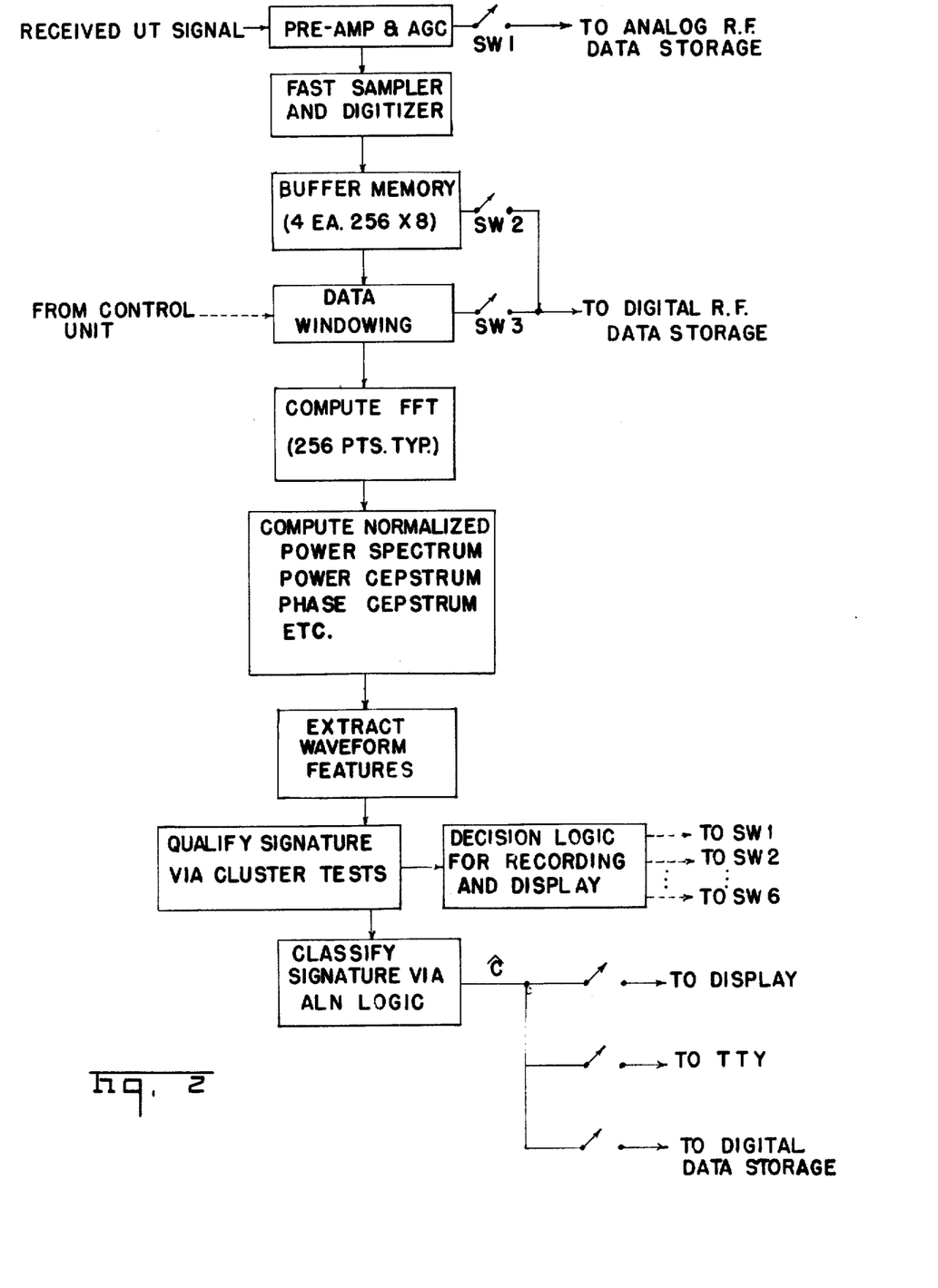
FIG. 2 is a diagram of signal conversion and processing within the NDE system.

The signal conversion and adaptive learning network (ALN) processing subsystem B, shown in further detail in FIG. 2, receives the RF output from the transducer in F and samples this waveform at a minimal rate of, for example, 10 million samples per second. The samples are then digitized using a minimum word length of, for example, 8 bits. Time gating is then applied (under supervision of the control unit A) to select the portions of the waveform that are to receive further analysis, and these are stored in, for example, four each, 256-word buffers. The contents of these buffers may be written into the portable digital memory D under supervision of the control unit A. From this memory, the information may be retrieved for display presentation at C and/or for transmission to a remote recorder at D'. Averaging of the waveform samples may also be used to minimize random noise components. A Fast Fourier Transform (FFT) is next taken (typically for 256 data points within a buffer "window"). The resulting Fourier coefficients are used to determine the normalized power spectrum of the waveform within the time window of interest. Further calculations are performed within the processor to obtain the power cepstrum and the phase cepstrum. Signal features of these spectral and cepstral functions are then extracted. The algorithms for feature extraction employ normalized band power (e.g., histogram) shape (e.g., amplitudes, durations, and intervals), and other mathematical and statistical descriptions, such as average and higher moments. These are well known in the art. Typical uses of a feature set of this kind are presented in M. Bath, *Spectral Analysis in Geophysics*, New York: Elsevier, 1974; T. Y. Young and T. W. Calvert, *Classification, Estimation and Pattern Recognition*, New York: Elsevier, 1974; as well as the references listed hereinbelow.

The features having been extracted, the distance between the feature vector and each of several previously-learned cluster cells is then computed. These distances are normalized, so that the smallest distance indicates which cell is nearest in feature space to the instant measurement. If this nearest cell contains the instant measurement, the signature is "qualified." Generally, a "qualified" signature is one that is strongly similar to either the signatures of previously seen defects or of previously seen benign scatterers. If strongly similar to the signatures of other known defects, the feature vector information is conveyed to the ALN discrimination function logic. There a more precise classification of the type, size, orientation, and location of the defect is determined. However, if the windowed signature is strongly similar to that of benign scatterers, or is free of any substantive indication of back-scattered energy, no classification is computed. A third instance may arise when the feature vector has ambiguous parameter values. In these cases, the inspector is alerted via the display unit, and the ALN logic is used to identify a "possible" flaw category. The above is set forth in detail in an application of A. N. Mucciardi and R. Shankar, Ser. No. 694,546, filed June 10, 1976, for System for Measurement of Subsurface Fatigue Crack Size, now U.S. Pat. No. 4,052,889, which is incorporated by reference.

A complete discussion of the cluster screening synthesis method may be found in A. N. Mucciardi, "An Automatic Clustering Algorithm and Its Properties in High-Dimensional Spaces," *IEEE Trans. of Systems, Man and Cybernetics*, Vol. SMC-2, No. 2, April 1972, pp. 247–254; and A. N. Mucciardi, "Information Filtering Using the CLUSTER Algorithm," *Proc. Computer Image Processing and Recognition Conference*, Univ. of Missouri, Columbia, June 1972, Vol. 2, pp. 15-3-1 to 15-3-8.

The ALN modeling synthesis method is discussed in:
L. O. Gilstrap, Jr., "Keys to developing Machines with High-Level Artificial Intelligence," Paper 71-DE-21, *The American Society of Mechanical Engineers, Design Engineering Conference and Show*, New York, New York, Apr. 19–22, 1971, A. G. Ivakhnenko, "Polynomial Theory of Complex Systems" *IEEE Transactions on Systems, Man, and Cybernetics*, Vol. SMC-1, No. 4, pp. 364–378, October 1971, R. L. Barron, "Adaptive Transformation Networks for Modeling, Prediction, and Control," *Proc. IEEE/ORSA Joint National Conference on Major Systems*, Anaheim, CA, Oct. 25–26, 1971, A. N. Mucciardi, "Neuromime Nets as the Basis for the Predictive Component of Robot Brains," *Cybernetics, Artificial Intelligence, and Ecology*, Robinson and Knight, (eds.), Spartan Books, 1972, pp. 159–193. (Presented at 4th Annual Symp. of American Soc. for Cybernetics, Washington, D.C., October 1970), A. N. Mucciardi, "Elements of Learning Control Systems with Applications to Industrial Processes", "*Proc.* 11*th IEEE Conference on Decision and Control*, New Orleans, La., Dec. 13–15, 1972, pp. 320–325, R. L. Barron, "Theory and Application of Cybernetic Systems: An Overview," *Proc. of the IEEE* 1974 *National Aerospace and Electronics Conference*, May 13–15, 1974, M. F. Whalen and A. N. Mucciardi, *Hypercomp TM—Upgraded Classifier, Part I: Synthesis of Nonlinear Adaptive Learning Network Seismic Target Classifier*, Adaptronics, Inc. Contract No. DAAK02-74-C-0322, USA Mobility Equipment Research and Development command, March 1975, R. L. Barron, "Applications of Learning Networks in Computer Aided Prediction and Control" Paper MS75-515, *Society of Manufacturing Engineers, CAD/CAM III Conference and Exposition*, Chicago, Illinois, Feb. 10–13, 1975.

R. L. Barron, "Learning Networks Improve Computer-Aided Prediction and Control," *Computer Design*, August 1975.

K. A. Augustyn, "Manufacturing Applications of Adaptive Learning Networks," Paper MS76-816, *Society of Manufacturing Engineers, SME Southwestern Tool Show*, Houston, Texas, Jan. 27, 1976, M. F. Whalen, J. D. Sanders, A. N. Mucciardi, *Performance Evaluation of Nine Candidate REMBASS Single-Target Classifiers*, Adaptronics, Inc. Contract No. DAAK02-74-C-0322, USA Mobility Equipment Research and Development Command, Feb. 20, 1976.

Adaptronics, Inc., "Empirical Design of Sensor Logic," Paper Presented at Second Symposium on Design, Testing, and Deployment of Unattended Ground Sensors, Waterways Experiment Station, Vicksburg, Miss., May 11–12, 1976, A. N. Mucciardi, M. F. Whalen, J. D. Sanders, R. L. Barron, "Six-Class Seismic/Acoustic Signal Classification Using Adaptive Polynomial Networks," *Proc. IEEE Int'l. Conf. on Cybernetics and Society*, Washington, D.C., Nov. 1–3, 1976, pp. 722–726, The signal processor is fabricated from CMOS and CMOS/SOS components to achieve minimum sensitivity to electromagnetic fields in the test environment. It uses LSI circuitry, most particularly a multiplier-accumulator component. The LSI Circuitry provides floating-point arithmetic with (nominally) 16 bits for the mantissa and 8 bits for the exponent. With the LSI circuitry, fewer than 75 integrated circuits are used for realization of the signal processor. Signal conversion at the required sampling rate is accomplished via an 8-bit, 100-nanosecond conversion time, A to D converter. For still higher sampling rates, CCD technology is employed.

The basic device in the portable display C is a high-persistence CRT with alphanumeric interface. The signal process causes the display to alert the inspector whenever an ambiguous signature is received. The inspector then has several options:

(1) He may command the instrument to inspect the region of the ambiguous echo from a variety of probe positions and angles to see if these produce an unambiguous classification.

(2) He may command the system to display the time waveform or power spectrum of the present or a prior waveform so that he may participate in evaluation of the signature. (The inspector can have contextual information available to him that is not available to the instrument.)

(3) In lieu of or in addition to (1) and (2) above, the inspector or remote observer may command the system to write information into bulk data storage D of D'. These data may be processed off-line, or they may be compared with test data obtained at a future inspection to determine if the region of a questionable echo has undergone any change between inspections. The printer is a miniature printer of the type used in commercial desk calculators. Alternatively, printing may be accomplished via a Teletyper or equivalent unit when such is attached electrically to the instrument.

Digital storage of the ultrasonic testing (UT) waveforms, including the emitted pulse and received echo(s), is provided by means of a portable floppy disk, bubble memory, CCD memory, or other random access memory unit D capable of storing at least 50 kilobytes and, optionally, via a remote recorder D.

The use of ALN signal processing to screen significant UT echoes from the many that can be properly ignored greatly reduces or eliminates the data storage needed when the NDE system is in operational use. However, substantial amounts of data must be logged to build the data base for ALN design and evaluation, because these data must include many echoes from the benign scatterers as well as from defects. Because of capacity limitations and the requirement for long recording duration, the portable recorder is not generally suitable for logging the design data base. Therefore, during in-plant data base acquisition, the NDE system is connected via an electrical cable to remote bulk-data storage apparatus D'.

Remote recording is used to obtain high recording rates (approaching 4 MBPS) combined with high capacity (up to 60-minute recording duration). The alternatives for this remote storage include longitudinal tape recorders such as the Honeywell 5620C and Bell & Howell 4020 digital recorders (2 MBPS for 15 minutes or 500 kBPS for 60 minutes) and helical-scan video recorders adapted for digital recording. The following is an example of the system in on-line operation with reference to the circuit block diagram of FIG. 3 wherein the dotted boxes correspond to the boxes of FIG. 1. Assuming the system is measuring for cracks and flaws in a pipe, the transducer scanning mount 52 will be mounted on the pipe under test. The operator will then turn on the remote system D' and close the system reset switch 54. The CPU controller 1 will now run a diagnostic test of the entire system under control of the program therein to see if there are any detectable malfunctions and display this in the alpha-numeric display 15 via the bus driver 4, UART 18 which is a serial to parallel converter, interface 17, and display interface 16. This entire procedure is provided in accordance with a program in the monitor ROM 9 which will be discussed later. The operator then provides information into the keyboard 21 as to the specific parameters required for the test to be run. This information is transmitted to the CPU controller 1 via the keyboard encoder 20, interface 19, UART 18, and bus driver 4.

Figure 3A:
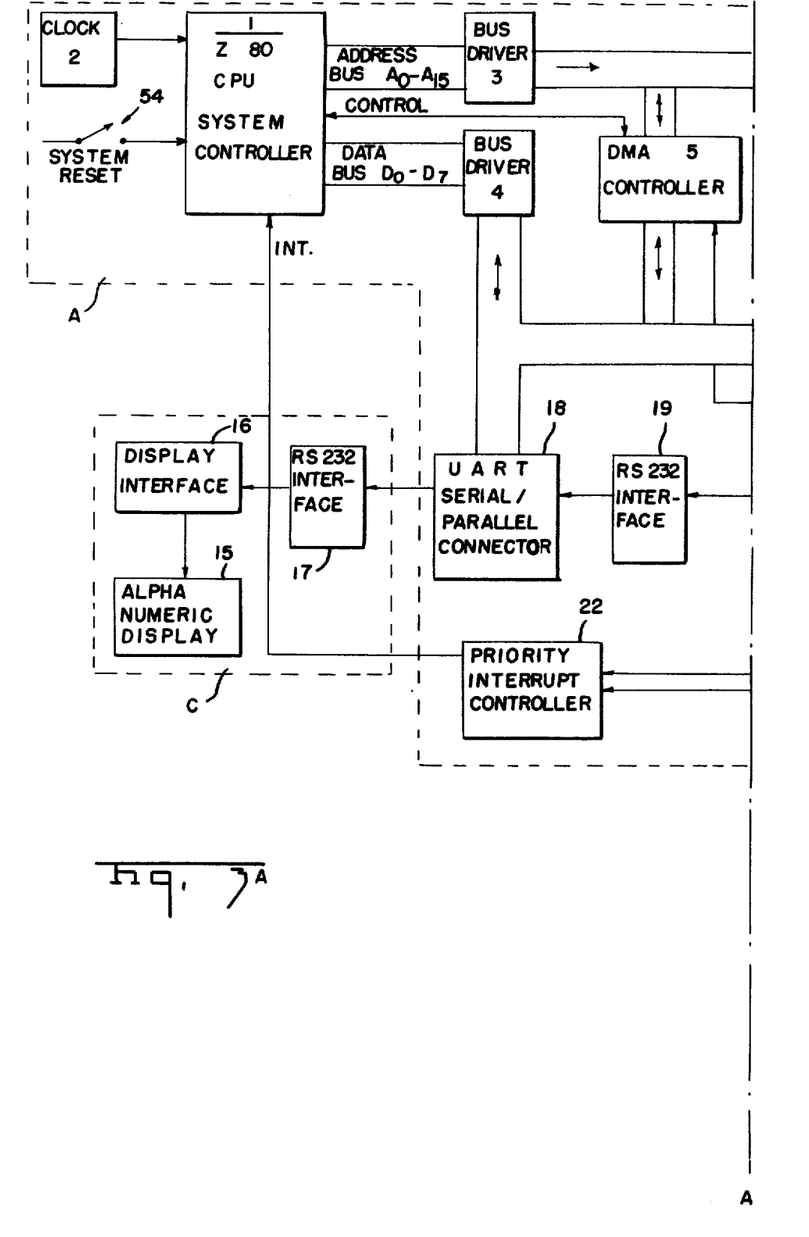

These parameters will be stored in the system RAM 7 via the RAM address decoder 6 and the bus driver 3 via the buffered address bus. The program stored in the scan sequence ROM 10 will then use the parameters just read into the system RAM 7 in order to position the transducer scanning mount 52 via values read into the latches and counters 37, 38, and 39 from RAM 7 which will proceed to the counters therein and drive the driving amplifiers 40, 41, and 42 which step the stepping motors 43, 44, and 45 to position the mount 52 in three degrees of freedom. The position of the transducer scanning mount 52 is then read back into CPU via shaft encoders 49, 50, and 51 and the I/O ports 46, 47, and 48 and is stored in system RAM 7 and compared with the location that was desired from the keyboard. This is compared by the CPU 1 and any errors are corrected using the scan sequence ROM 10 to properly position the transducer scanning mount 52. This correction via the sequence scan ROM 10 is provided when the ROM 10 is addressed through the ROM address decoder 8. This signal is read back from the I/O ports via the buffered data bus and the bus driver 4 to the CPU 1. The transducer mount is now properly positioned and the system is now ready to accept data. The program ROM 11 then uses the function parameters that were stored in system RAM 7 to send the function parameter information to the CPU 24 via the I/O port 35. Header information is written by the CPU 1 through bus driver 4 and buffered data bus onto the bulk storage device 14 via tape or disk interface 12 and tape or disk controller 13. This header information includes the initial position of the scanner mount and the incremental position the mount will take throughout the system as well as the functions that have been sent to the signal processer 24. The CPU 1 then signals the CPU 24 via the bus driver 4, buffered data bus, and I/O port 35. Signal processer 24 then initializes the transducer 34 with parameters it needs to run. Then the transducer starts pulsing and takes data which are transmitted to the gating and timing circuit 32 and sent directly to A to D converter 30. The inspector may use an optional scope display 53 connected to the output of the transducer 34 to make decisions about the initial parameters which are read in on keyboard 21. The CPU 24 must also indicate through I/O port 31 to the gating and timing circuit 32 which parameters it needs to gate and time the data from the transducer 34. The data from the A to D converter 30 are then sent out to the I/O port 29 on the data bus to the buffer memory 28; then the signal processor 24, using its processing functions in ROM 27, will process the data in the buffer memory 28, using its multiplier/accumulator, 25, and the data are sent back into the buffer memory 28. Address decoder 26 is used to set up the addresses whenever memory 28 or processing ROM 27 are addressed. The CPU 24 will signal the CPU 1 that the data have been taken. Any flaw data are sent from the buffer memory 28 via the data bus, I/O port 35, buffered data bus to the UART 18 interface 17, display interface 16, and alpha-numeric display 15 to indicate those flaws to the inspector. The raw data and the processed data from the buffer memory 28 are also read out through the data bus via the DMA controller 5, the buffered data bus, to the bulk storage device 14, via its interface and controller 12 and 13. I/O port decoder 36 is referenced each time and an I/O port is referenced and used. The control line from the I/O port decoder is used to send an enabling pulse to the I/O port which is being referenced. The monitor ROM 9 holds the sequence of instructions necessary to run the system and to communicate with the displays and the keyboards. At any time during the operation of the system, the inspector, via the keyboard, has the option to interrupt the system, wherein the keyboard sends logic signals through the priority interrupt controller 22 to the CPU 1, and the instructions being carried out at that time are terminated to handle whatever interrupt the inspector wants. An interrupt can also be signaled from the signal processor 24 to the CPU 1 if, for some reason, in its functioning, it requires immediate attention. The Clock 2 is an input to CPU 1 which sets the rate at which the CPU 1 handles its functions. Clock 23 is an input to the CPU 24 and sets its function rate. After a scanning sequence is completed, the CPU 1 then repositions the transducer scanning mount 52 as per the previous sequence, and the entire set of instructions is repeated for each position of the transducer until all programmed positions have been scanned. The system also has an automatic mode whereby the operator at the keyboard has the option of not specifying any one of the initial parameters, but simply having the program from the program ROM 11 take over and initialize those parameters for him. This could be used, for example, where the set of parameters is the same as that used in a prior test. The parameters in the program ROM 11 can be placed there initially, "burned in", or by other means, all of which are well known in the art.

As stated above, the microprocessor chips 1 and 24, which provide the system control and the system signal processing functions, respectively, operate from programs which are stored in the RAM and ROM chips of the system. The operation of these two microprocessors will now be discussed with reference to FIG. 4, which is a flow diagram of their operation.

Figure 4A:
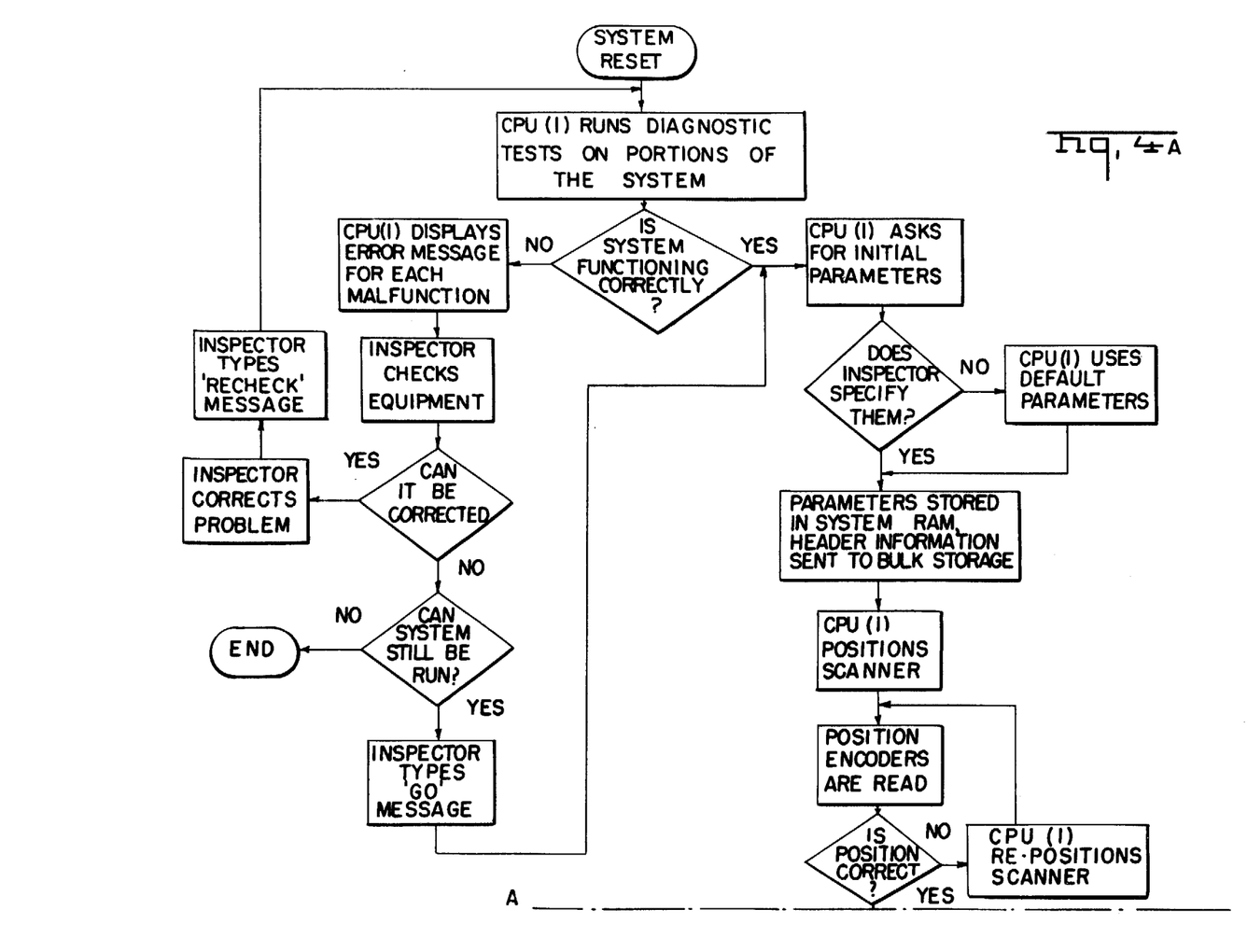
FIGS. 4A and 4B, is a flow chart of the operation of controller 1 and signal processor 24 of FIG. 3.
Figure 4B:
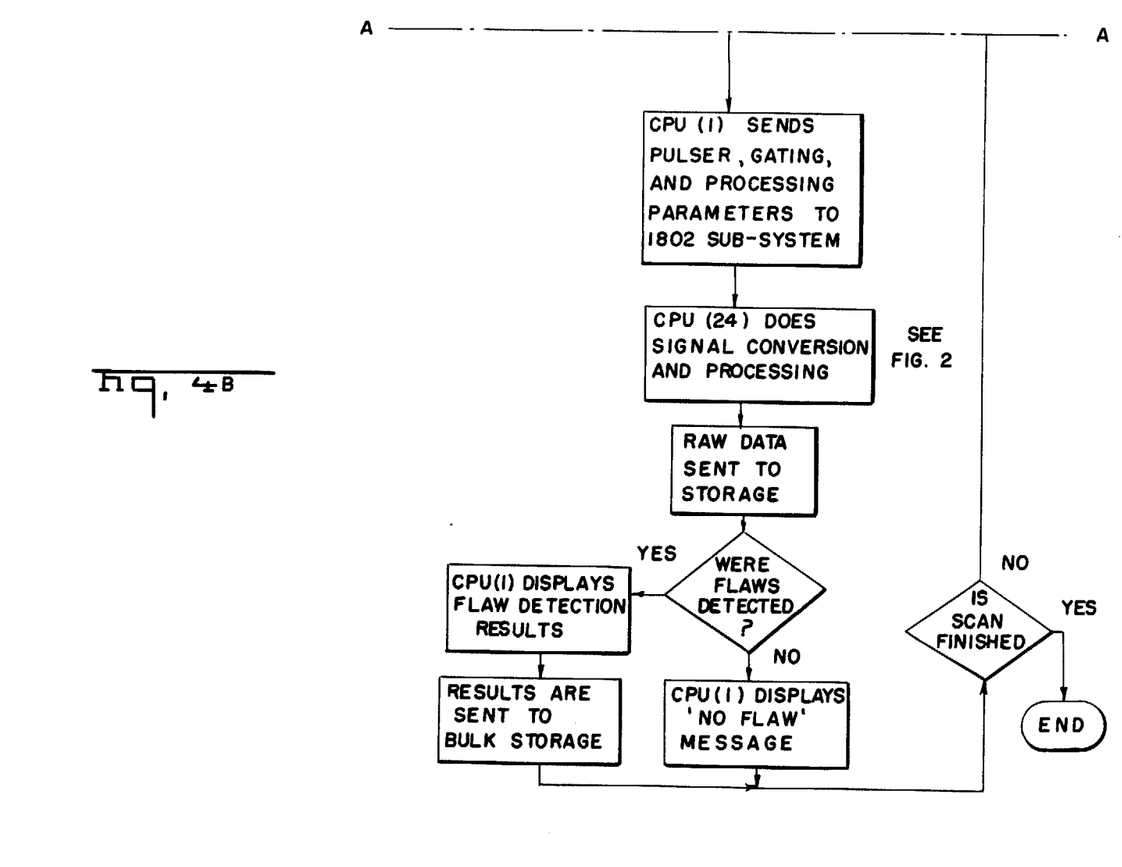
Figure 7B:
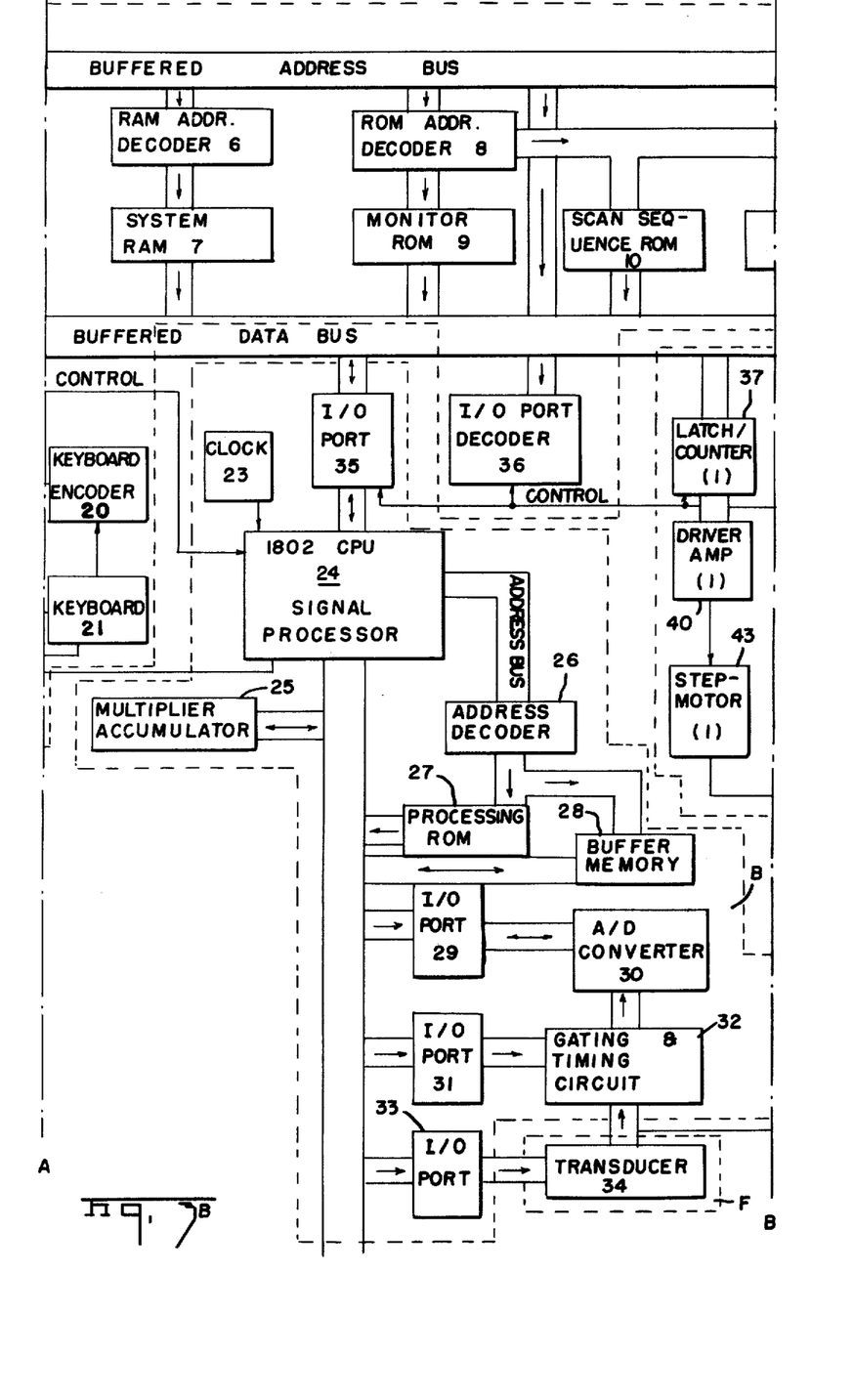
Figure 7C:
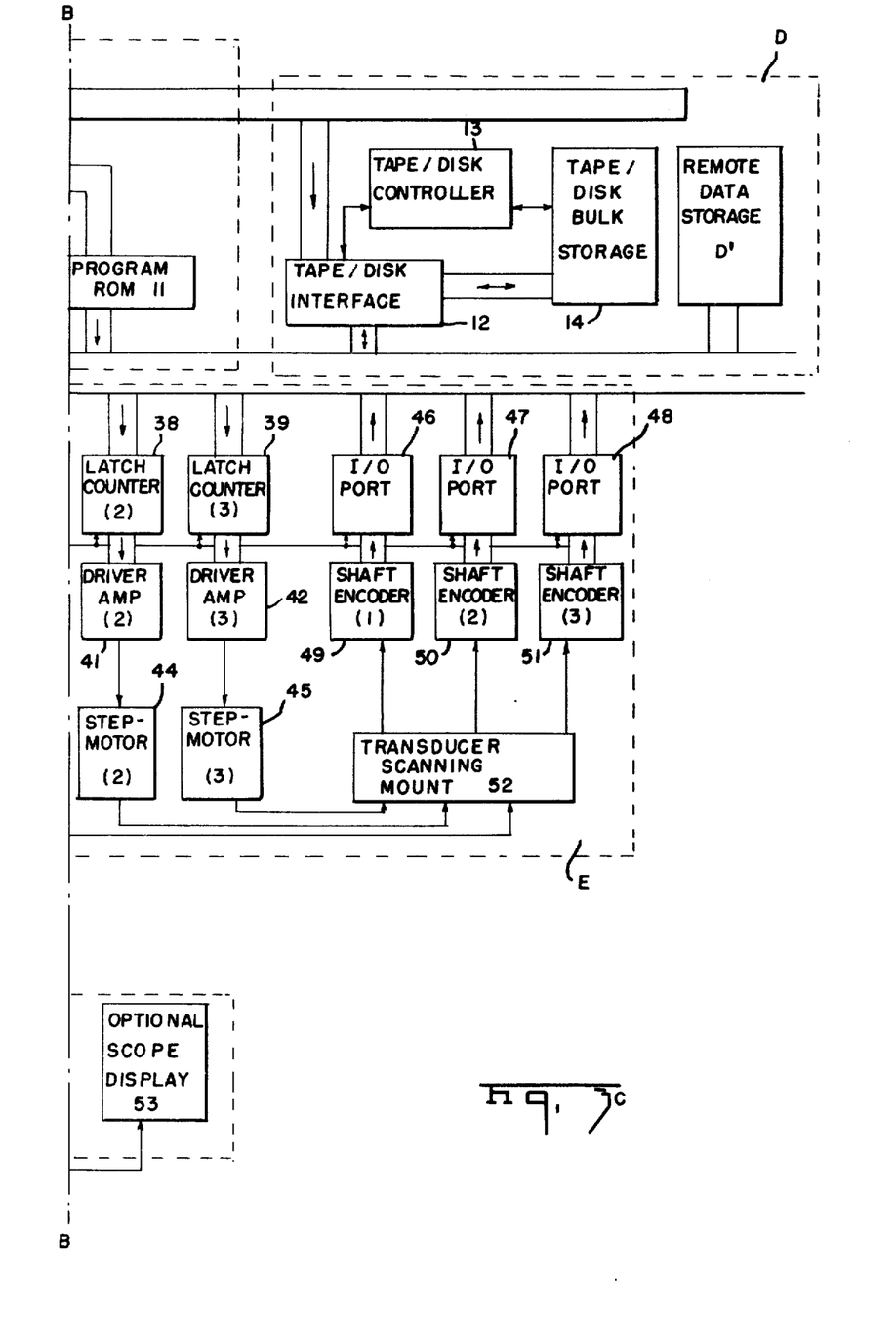

The flow diagram starts off with a system reset which is provided when the switch 54 of FIG. 3 is closed. The system controller 1 then runs diagnostic tests on portions of the system. These diagnostic tests or routines include stepping the motors 43, 44, and 45 backward and forward and verifying the movements by reading out the shaft position encoders 49, 50, and 51. The unit also verifies the correct function of the system random access memory 7 and bulk storage device 14 by writing to and reading back from them. Any deviations from normal operation are displayed to the inspector via display 15 for appropriate action by him, if possible. Therefore, the next block in the flow chart, which states "is system functioning correctly?" is a result of these diagnostic tests. If the system is not functioning correctly, the controller 1 (CPU 1) displays an error message for each malfunction on the alpha-numeric display 15. The inspector then checks the equipment and determines if the malfunction can be corrected. If it can be corrected, the inspector corrects the problem and the inspector then types a "recheck" message into the keyboard 21, whereupon the entire procedure starts from the beginning. If the system cannot be corrected, the question is then asked whether the system can be run. If the answer is "no," the operator shuts down the system and the operation comes to an end. If the answer is "yes," the inspector types "go" into the keyboard 21, and the system proceeds in the same manner as it does if the system were functioning correctly. However, the system is capable of modifications to its operating sequence due to slight non-correctable problems of certain units. For instance, if the motors function in the forward direction only, the stepping sequence to a specified position does not use any reverse steps. In the case of a malfunctioning ROM, the stored programs are available from the bulk storage device and are read into RAM and executed from that memory location.

The CPU 1 now asks for initial parameters. The questions are part of the program stored in program ROM 11, and these questions are displayed on the alpha-numeric display 15. If the answer is "yes," the operator types instructions into the keyboard 21, and if the answer is "no," the CPU 1 uses default parameters which are parameters stored in the program ROM 11. The parameters stored in the system RAM 7 are the parameters which have been typed into the keyboard by the inspector. Header information, which includes the parameters read into storage for a particular evaluation, are then sent to the bulk storage 14.

The CPU 1 then positions the scanner mount 52 via the stored parameters in the scan sequence ROM 10. The shaft encoders 49, 50, and 51 are then read as to their position. If the position is incorrect, the CPU 1 repositions the scanner 52 and the position of the encoders is reread and rechecked. If the position is correct, the CPU 1 sends pulser, gating, and processor parameters to the CPU 24 subsystem. The CPU 24 then does signal conversion and processing in accordance with the procedure set forth in FIG. 2, which is explained above as well as in the prior application of Mucciardi and Shankar (referenced above). The digitized raw data from buffer memory 28 are sent to storage unit 14.

The question is then asked whether flaws were detected. If the answer is "yes," the CPU 1 displays the flaw detection results and the results are then sent to the bulk storage 14. The algorithms used in the discrimination programs provide for several alternate outputs, depending upon the data obtained. If the data were very clear and fit into a cluster pattern precisely, then a definite evaluation is given as to the type, size, and location of the flaw. In some instances the data do not fit clearly, and ambiguous results thus occur, and the operator is then notified of this situation. If the answer was "no," that flaws were not detected, the CPU 1 displays "no flaws" on the display 15. In either case, the question is then asked whether the scan is finished, and if the answer is "yes," the test comes to an end. If the answer is "no," the CPU repositions the scanner and the positions of the encoders are again read with the entire cycle therefrom being repeated.

APPENDICES

Appendix A is a list of the principal hardware contents of each block in FIG. 3.

Appendix B is an example of the use of the cluster screening method in a representative signal-processing application.

APPENDIX A

The following is a list of the hardware contents of each box in FIG. 3:

| Block No | Name | Manufacturer | Chip | Function |
|---|---|---|---|---|
| 1 | CPU | Zilog | Z80 | System Controller |
| 2 | Clock | TTL IC | 74123 | Clock Input to Z80 |
| 3 | Bus Driver | TTL IC | 74367 | Drive and Buffer Busses |
| 4 | Bus Driver | TTL IC | 74367 | Drive and Buffer Busses |
| 5 | DMA Controller | Intel | 8257 | Direct Memory Access Controller |
| 6 | Address Decoder | TTL IC | 74154 | Decode RAM Addresses |
| 7 | RAM | Intel | 8102A-4 | Random Acess Memory |
| 8 | Address Decoder | TTL IC | 7442 | Decode RAM Addresses |
| 9,10,11 | ROM | INTEL | 2708 | Read Only Memory |
| 12 | Tape Interface | Microvox | 05-024 | Hardware Interface |
| 13 | Tape Controller | Microvox | 05-034 | Software Interface |
| 14 | Tape Storage | Microvox | 90-003 | Bulk Storage |
| 15 | Alpha-Numeric Display | Termiflex | HT/4 | Alpha-Numeric Display |
| 16 | Display Interface | Termiflex | HT/4 | Interface FSR Display |
| 17,19 | RS232 Interface | TTL IC | 74188, 74189 | Line Drivers and Receivers |
| 18 | UART | Intel | 8251 | Serial/Parallel Converter |
| 20 | Keyboard Encoder | Termiflex | HT/4 | Encode Keys |
| 21 | Keyboard | Termiflex | HT/4 | Keyboard |
| 22 | Priority Interrupt Controller | Intel | 8214 | Control Interrupts |

-continued

| Block No | Name | Manu-facturer | Chip | Function |
|---|---|---|---|---|
| 23 | Clock | TTL | Crystal | Clock Input to 1802 |
| 24 | CPU | RCA CDP | 1802 | Signal Processor |
| 25 | Multiplier/Accumulator | RCA | CMOS/SOS | Fast Multiplier |
| 26 | Address Decoder | RCA | CDP 18215 | Decode Addresses |
| 27 | ROM | RCA | CDP 1833 | Read Only Memory |
| 28 | RAM | RCA | CDP 18215 | Random Acess Memory |
| 29, 31, 33 | I/O Port | RCA | CDP 1852 | Input/Output Port |
| 30 | A/D Converter | RCA | | Analog to Digital Converter |
| 32 | Gating, Timing Circuit | RCA | | Gate and Time Signal |
| 35, 46, 47, 48 | I/O Port | Intel | 8212 | Input/Output Port |
| 36 | I/O Port Decoder | TTL IC | 74154 | Port Address Decoder |
| 37, 38, 39 | Latch/Counter | TTL IC | 7553, 74193 | Hold and Count Number |
| 40, 41, 31 | Drive Amp | TTL IC | 75450, 74123 | Pulse Stepping |
| 43, 44, 45 | Stepping Motors | Any Suitable | | Move Transducers |
| 49, 50, 51 | Shaft Encoders | Available from Babcock & Wilcox | | Indicate Position |
| 52 | Scanning Mount | Available from Babcock & Wilcox | | Holds Transducer |
| 53 | Optional Scope | Any Oscilloscope | | Spectral Viewing |
| 54 | System Reset | Switch | | System Reset |
| 34 | Transducer | Any of Suitable Frequency | | Send/Receive Signals |

For epoch n of the waveform received by the system in this application (n=1, 2, ..., 32) the real and imaginary coefficients computed by the FFT* are denoted $(CR)_{n,j}$ and $(CI)_{n,j}$, respectively, where j=1, ..., 16. The normalized spectral power levels for the epoch are:

$$P_{n,j} = [(CR)_{n,j}^2 + (CI)_{n,j}^2] \bigg/ \sum_{j=1}^{16} [(CR)_{n,j}^2 + (CI)_{n,j}^2]$$

and the discrete frequencies of these spectral power levels are (7.8125 j) Hz.
*Fast Fourier Transform (FFT).

The X (single-epoch) feature vector has seven components, computed as follows:

$x_{n,1} = P_{n,1}$
$x_{n,2} = P_{n,2}$
$x_{n,3} = P_{n,3}$
$x_{n,4} = P_{n,10}$
$x_{n,5} = P_{n,13}$
$x_{n,6} = P_{n,16}$ and $$x_{n,7} = \begin{cases} 1 & \text{if } 3\sum_{j=2}^{8} P_{n,j} \geq 2 \\ 0 & \text{otherwise} \end{cases}$$

If $x_{n,7}$ is observed to be 1, it is highly probable that a class D event has been detected.

The first step in qualifying the unknown signature is to determine if its feature vector lies within or at least near to one of the major cluster cells that existed in the design data base. To make this determination, the fol-

TABLE I

MAJOR $X_1$ CLUSTERS FOUND IN 2,532 SEISMIC EPOCHS

| Cluster Identification | Cluster Rank | Total Hits No. | % | TV Hits No. | % | WV Hits No. | % | FF Hits No. | % | BG Hits No. | % | p(TV/M) | p(WV/M) | p(FF/M) | p(BG/M) |
|---|---|---|---|---|---|---|---|---|---|---|---|---|---|---|---|
| (201) | 1 | 374 | 14.8 | 63 | 6.0 | 127 | 19.4 | 184 | 68.2 | 0 | 0 | .168 | .340 | .492 | 0 |
| (129) | 2 | 203 | 8.0 | 46 | 4.4 | 19 | 2.9 | 0 | 0 | 138 | 24.6 | .227 | .094 | 0 | .680 |
| (54) | 3 | 163 | 6.4 | 18 | 1.7 | 97 | 14.8 | 0 | 0 | 48 | 8.5 | .110 | .595 | 0 | .294 |
| (169) | 4 | 114 | 4.5 | 38 | 3.6 | 17 | 2.6 | 0 | 0 | 59 | 10.5 | .333 | .149 | 0 | .518 |
| (16) | 5 | 102 | 4.0 | 47 | 4.5 | 27 | 4.1 | 28 | 10.4 | 0 | 0 | .461 | .265 | .275 | 0 |
| (17) | 6 | 91 | 3.6 | 63 | 6.0 | 19 | 2.9 | 0 | 0 | 9 | 1.6 | .692 | .209 | 0 | .099 |
| (15) | 7 | 75 | 3.0 | 45 | 4.3 | 18 | 2.7 | 0 | 0 | 12 | 2.1 | .600 | .240 | 0 | .160 |
| (84) | 8 | 61 | 2.4 | 9 | 0.9 | 25 | 3.8 | 0 | 0 | 27 | 4.8 | .148 | .410 | 0 | .443 |
| (62) | 9 | 60 | 2.4 | 23 | 2.2 | 11 | 1.7 | 0 | 0 | 26 | 4.6 | .383 | .183 | 0 | .433 |
| (161) | 10 | 56 | 2.2 | 22 | 2.1 | 13 | 2.0 | 0 | 0 | 21 | 3.7 | .393 | .232 | 0 | .375 |
| (20) | 11 | 42 | 1.7 | 14 | 1.3 | 5 | 0.8 | 23 | 8.5 | 0 | 0 | .333 | .119 | .548 | 0 |
| Totals | | 1,341 | 53.0 | 388 | 37.2 | 378 | 57.6 | 235 | 87.0 | 340 | 60.5 | | | | |
| All Others | | 1,191 | 47.0 | 656 | 62.8 | 278 | 42.4 | 35 | 13.0 | 222 | 39.5 | | | | |
| Grand Totals | | 2,532 | 100.0 | 1,044 | 100.0 | 656 | 100.0 | 270 | 100.0 | 562 | 100.0 | | | | |

APPENDIX B

EXAMPLE OF CLUSTER SCREENING METHOD IN SIGNAL-PROCESSING APPLICATION

Table 1 below summarizes the major seven-dimensional, single-epoch feature vector (X) clusters found by the Mucciardi-Gose clustering algorithm in a representative cluster screening application. It is seen that the 1$\sigma$ dimensions of the 11 most populous clusters contain 53 percent of the single-epoch feature vectors representing 2,532 seismic epochs from the F and S data subsets.

lowing normalized distance metric is computed for each of the major clusters $$D^2 = \sum_{i=1}^{7} \frac{(x_{n,i} - \bar{x}_i)^2}{S_i^2}$$

where:

$x_{n,i}$ = one of seven features from $n^{th}$ single-epoch vector X
$\bar{x}_i$ = mean value of $x_i$ for this cell
$S_i$ = shape factor of $x_i$ for this cell The mean value ($\bar{x}_i$) and shape factor ($S_i$) are constants stored in read-only memory. Table 2 below gives the values computed by Adaptronics for these constants, using the CLUSTR algorithm (Mucciardi and Gose). The shape factors ($S_i$'s), which are proportional to, but always greater than if not equal to, the standard deviations of the corresponding variables in the cells, account for the fact that cells have different sizes: although an observation may be equally distant from the center of two different cells, it is actually closer on a relative basis to the center of the larger cell.

To avoid squaring and division, the classifier should store the inverse squares of the shape factors.

$$D^2 = \sum_{i=1}^{7} C_i(x_{n,i} - \bar{x}_i)^2$$

in which $$C_i = 1/S_i^2$$

In summary, the value of $D^2$ is computed once for each major cell of interest, using the (single-epoch) feature vector.

Considering the sizes of the different-cells, the point X is nearest to that cluster cell for which $D^2$ is smallest. Accordingly, as each of the first 11 distance metrics is computed (for Cells 1 through 11), this metric is compared with the smallest value of $D^2$ already found for the same epoch, thereby determining the identity of the nearest cell once the 11th $D^2$ has been computed.

Having identified the nearest of the first 11 cells by this process, the following seven tests are performed (i = 1, . . . , 7):

$$\text{Is} \, |x_{n,i} - \bar{x}_i| \leq S_i?$$

TABLE 2
CENTROIDS AND SHAPE FACTORS ($S_i = 2\sigma_i$) OF THE 13 MAJOR $X_1$ CLUSTER CELLS

| Cell | $\bar{x}_1$ | $\bar{x}_2$ | $\bar{x}_3$ | $\bar{x}_4$ | $\bar{x}_5$ | $\bar{x}_6$ | $\bar{x}_7$ |
|---|---|---|---|---|---|---|---|
| | | | Centroids | | | | |
| 1 | .06946 | .10374 | .06726 | .20150 | .07597 | .02904 | 0.00000 |
| 2 | .03405 | .02747 | .07769 | .02698 | .01461 | .01202 | 1.00000 |
| 3 | .11043 | .01919 | .01951 | .01313 | .01831 | .00669 | 0.00000 |
| 4 | .03080 | .24724 | .07396 | .03417 | .02793 | .04136 | 1.00000 |
| 5 | .65587 | .08497 | .06624 | .00675 | .00566 | .00583 | 0.00000 |
| 6 | .18721 | .02867 | .02341 | .11022 | .01548 | .08234 | 0.00000 |
| 7 | .39258 | .27152 | .07347 | .01444 | .00802 | .00759 | 0.00000 |
| 8 | .25658 | .13891 | .07524 | .03267 | .03040 | .11625 | 0.00000 |
| 9 | .04522 | .06694 | .03265 | .02987 | .07702 | .06048 | 0.00000 |
| 10 | .18670 | .10105 | .06784 | .02244 | .08080 | .01047 | 0.00000 |
| 11 | .09857 | .29357 | .18648 | .00977 | .00779 | .00737 | 1.00000 |
| 12 | .02377 | .02657 | .03107 | .13297 | .01438 | .01520 | 0.00000 |
| 13 | .06202 | .13491 | .30502 | .00954 | .00657 | .00697 | 1.00000 |

| Cells | $S_1$ | $S_2$ | $S_3$ | $S_4$ | $S_5$ | $S_6$ | $S_7$ |
|---|---|---|---|---|---|---|---|
| | | | Shape Factors | | | | |
| 1 | .13003 | .17438 | .11238 | .29870 | .14631 | .07393 | .50000 |
| 2 | .07321 | .04422 | .15741 | .04342 | .02195 | .02569 | .50000 |
| 3 | .21833 | .03327 | .03714 | .01855 | .02928 | .01656 | .50000 |
| 4 | .04488 | .30064 | .11782 | .04920 | .03787 | .07385 | .50000 |
| 5 | .26364 | .09841 | .11208 | .01442 | .01316 | .01792 | .50000 |
| 6 | .27375 | .04320 | .04217 | .17743 | .02361 | .13794 | .50000 |
| 7 | .21983 | .07841 | .08832 | .03292 | .01423 | .01759 | .50000 |
| 8 | .33629 | .21408 | .13364 | .06073 | .05860 | .20197 | .50000 |
| 9 | .06813 | .09654 | .05169 | .03822 | .06244 | .09562 | .50000 |
| 10 | .17790 | .10007 | .10210 | .03526 | .15208 | .02334 | .50000 |
| 11 | .15244 | .46054 | .31506 | .02117 | .01874 | .02028 | .50000 |
| 12 | .04470 | .08322 | .07671 | .26134 | .02249 | .03082 | .50000 |
| 13 | .08821 | .21222 | .53564 | .02520 | .01686 | .01935 | .50000 |

If all seven questions are answered in the affirmative, the point X is viewed as being a member of cell M, the cell for which $D^2$ is minimum. Additionally, if membership in one of the first 11 cells is established, a further test is made for possible membership in either Cell 12 or Cell 13.

In the following, the terminology Probability State Vector (PSV) is used to denote a four-component vector of a posteriori probabilities, e.g.

$$PSV = (p_A, p_B, p_C, p_D, p_E)$$

The components of this vector are defined as follows:
$p_A$ = single-epoch probability that the waveform is produced by a disturbance of type A
$p_B$ = single-epoch probability that the waveform is produced by a disturbance of type B etc.

If none of the first 11 major cluster cells "captures" the feature vector, the PSV becomes a null vector for the epoch in question. However, when X is "captured" by a given cell M, a table look-up is performed to determine the PSV. Table 3 contains the information required for this table look-up in the representative application.

TABLE 3
Components of Probability State Vector and $p_{ER}$ for the 13 Major $X_1$ Cluster Cells

| Cells | $p_A$ | $p_B$ | $p_C$ | $p_D$ | $p_E$ |
|---|---|---|---|---|---|
| 1 | .6000 | .2400 | .1600 | −0.0000 | −0.0000 |
| 2 | .4610 | .2650 | 0.0000 | .2750 | −0.0000 |
| 3 | .6920 | .2090 | .0990 | −0.0000 | −0.0000 |
| 4 | .3330 | .1190 | 0.0000 | .5480 | −0.0000 |
| 5 | .1100 | .5950 | .2940 | −0.0000 | −0.0000 |
| 6 | .3830 | .1830 | .4330 | −0.0000 | −0.0000 |
| 7 | .1480 | .4100 | .4430 | −0.0000 | −0.0000 |
| 8 | .2270 | .0940 | .6800 | −0.0000 | −0.0000 |
| 9 | .3930 | .2320 | .3750 | −0.0000 | −0.0000 |
| 10 | .3330 | .1490 | .5180 | −0.0000 | −0.0000 |
| 11 | .1680 | .3400 | 0.0000 | .4920 | −0.0000 |
| 12 | 0.0000 | 0.0000 | 0.0000 | 0.0000 | 1.0000 |
| 13 | 0.0000 | 0.0000 | 0.0000 | 0.0000 | 1.0000 |

Though the invention has been described with respect to a specific preferred embodiment thereof, many variations and modifications will immediately become apparent to those skilled in the art. It is therefore the intention that the appended claims be interpreted as broadly as possible in view of the prior art to include all such variations and modifications.

We claim:

1. A method of nondestructive testing and evaluation of signals representative of characteristics of an object under test, which comprises the steps of:
    (a) providing a data base comprising data indicative of predetermined characteristics of said object under test,
    (b) positioning transducer means relative to said object under test in response to data in said data base,
    (c) receiving an energy waveform emanating from said object under test at said transducer means after said positioning,
    (d) performing an analysis at selected points on said waveform to extract waveform features thereof,
    (e) comparing the extracted waveform features of said analysis with said data base by a cluster test,
    (f) classifying said waveform features from said comparison, and
    (g) indicating the existence and parameters of said characteristics of said object under rest from said classifying.

2. A method as set forth in claim 1 wherein the results of said classification are stored.

3. A method as set forth in claim 2 wherein said energy waveform is stored.

4. A method as set forth in claim 3 wherein said received energy waveform is reflected from said object under test.

5. A method as set forth in claim 4 wherein said analysis performed in step (d) is at least one of a spectral and cepstral analysis.

6. A method as set forth in claim 3 wherein said analysis performed in step (d) is at least one of a spectral and cepstral analysis.

7. A method as set forth in claim 1 wherein said energy waveform is stored.

8. A method as set forth in claim 1 wherein said received energy waveform is reflected from said object under test.

9. A method as set forth in claim 8 wherein said analysis performed in step (d) is at least one of a spectral and cepstral analysis.

10. a method as set forth in claim 1 wherein said analysis performed in step (d) is at least one of a spectral and cepstral analysis.

11. A test system for nondestructive evaluation of signals representative of characteristics of an object under test, which comprises:
 (a) transducer means for receiving energy waveforms from said object under test,
 (b) positioning means for positioning said transducer means relative to said object under test,
 (c) control means for controlling said positioning means,
 (d) means responsive to the waveforms received by said transducer and controlled by said control means to select a portion of said waveform,
 (e) means for selecting a predetermined number of points on the selected portion of said waveform and processing said points according to a predetermined format to provide predetermined waveform features,
 (f) means for comparing the waveform features with a known set of waveform features by a cluster test, and
 (g) means responsive to said comparison to provide characteristics of said object under test.

12. A test system as set forth in claim 11 wherein said transducer means are ultrasonic.

13. A test system as set forth in claim 12 wherein said control means includes storage means for storing a data base and storage means for storing instructions and said control means further includes means for evaluating said signal waveforms received by said transducer means and said means for selecting includes means to compute a cepstral spectrum, a power cepstrum and a phase cepstrum from said received signal waveforms.

14. A test system as set forth in claim 11 wherein said control means includes storage means for storing a data base and storage means for storing instructions and said control means further includes means for evaluating said signal waveforms received by said transducer means and said means for selecting includes means to compute a cepstral spectrum, a power cepstrum and a phase cepstrum from said received signal waveforms.

15. A method of nondestructive testing and evaluation of signals representative of characteristics of an object under test, which comprises the steps of:
 (a) providing a data base comprising data indicative of predetermined characteristics of said object under test,
 (b) positioning transducer means relative to said object under test in response to data in said data base,
 (c) receiving at least one energy waveform on at least one boundary of the object under test,
 (d) performing an analysis of at least one of selected points and selected portions of said waveform,
 (e) analyzing the results of said analysis relative to said data base by at least one of a cluster test and a waveform classifying procedure to indicate at least one of the existence of and parameters of said characteristics of said object under test, and
 (f) determining the desirability of storing at least one of and displaying at least one of said energy waveforms, said existence, said parameters and none of these.

16. A method as set forth in claim 15 wherein said classifying is performed by an adaptive learning network.

17. A method as set forth in claim 15 wherein said classifying procedure is performed by an adaptive learning network.

18. A test system for nondestructive evaluation of signals representative of characteristics of an object under test, which comprises:
 (a) transducer means for receiving energy waveforms from said object under test,
 (b) means for at least one of measuring and measuring and controlling the position of said transducer means relative to said object under test,
 (c) means responsive to the waveforms received by said transducer means and said means for measuring to select at least one of points and portions of said waveforms,
 (d) means for performing an analysis of at least one of said points and portions of said waveforms;
 (e) means for analyzing the results of said analysis by at least one of a cluster test and a waveform classifying procedure to indicate at least one of the existence of and parameters of said characteristics of said object under test, and
 (f) means for determining desirability of at least one of storing and displaying at least one of said energy waveforms, said existence, said parameters and none of these.

19. A system as set forth in claim 18 further including an adaptive learning network to perform said classifying procedure.

20. A method of nondestructive testing and evaluation of signals representative of characteristics of an object under test, which comprises the steps of:
 (a) providing a data base comprising data indicative of predetermined characteristics of said object under test,
 (b) positioning transducer means relative to said objects under test in response to data in said data base,
 (c) receiving at least one energy waveform on at least one boundary of the object under test,
 (d) performing an analysis of at least one of selected points and selected portions of said waveform, and
 (e) analyzing the results of said analysis relative to said data base by at least one of a cluster test and a waveform classifying procedure to indicate at least one of the existence of and parameters of said characteristics of said object under test.

21. A test system for nondestructive evaluation of signals representative of characteristics of an object under test, which comprises:

(a) transducer means for receiving energy waveforms from said object under test,
(b) means for at least one of measuring and measuring and controlling the position of said transducer means relative to said object under test,
(c) means responsive to the waveforms received by said transducer means and said means for measuring to select at least one of points and portions of said waveforms,
(d) means for performing an analysis of at least one of said points and portions of said waveforms; and
(e) means for analyzing the results of said analysis by at least one of a cluster test and a waveform classifying procedure to indicate at least one of the existence of and parameters of said characteristics of said object under test.

22. A system as set forth in claim 21 further including an adaptive learning network to perform said classifying procedure.

* * * * *